United States Patent [19]

Asher et al.

[11] Patent Number: 4,773,402
[45] Date of Patent: Sep. 27, 1988

[54] DORSAL TRANSACRAL SURGICAL IMPLANT

[75] Inventors: Marc A. Asher, Prairie Village, Kans.; Walter E. Strippgen, Golden, Colo.

[73] Assignee: Isola Implants, Inc., Golden, Colo.

[21] Appl. No.: 88,472

[22] Filed: Aug. 19, 1987

Related U.S. Application Data

[63] Continuation of Ser. No. 775,650, Sep. 13, 1985, abandoned.

[51] Int. Cl.⁴ .............................................. A61B 17/58
[52] U.S. Cl. ................... 128/69; 128/92 YM; 128/92 YP
[58] Field of Search ............... 128/69, 92 YM, 92 Z, 128/92 YP, 92 YF

[56] References Cited

U.S. PATENT DOCUMENTS

| | | | |
|---|---|---|---|
| 3,242,922 | 3/1966 | Thomas | 128/92 YM |
| 4,041,939 | 8/1977 | Hall . | |
| 4,047,523 | 9/1977 | Hall . | |
| 4,078,559 | 3/1978 | Nissinen | 128/69 |
| 4,085,744 | 4/1978 | Lewis et al. . | |
| 4,274,401 | 6/1981 | Miskew | 128/69 |
| 4,361,141 | 11/1982 | Tanner . | |
| 4,361,144 | 11/1982 | Slatis | 128/92 Z |
| 4,369,769 | 9/1983 | Edwards . | |
| 4,369,770 | 1/1983 | Bacal et al. . | |
| 4,382,438 | 5/1983 | Jacobs . | |
| 4,404,967 | 9/1983 | Bacal et al. . | |
| 4,411,259 | 10/1983 | Drummond | 128/69 |
| 4,422,451 | 12/1983 | Kalamchi | 128/69 |
| 4,433,676 | 2/1984 | Bobechko . | |
| 4,454,876 | 6/1984 | Mears | 128/92 YP |
| 4,569,338 | 2/1986 | Edwards | 128/92 B |
| 4,653,481 | 3/1987 | Howland | 128/92 YM |
| 4,655,199 | 4/1987 | Steffee | 128/69 |
| 4,686,970 | 8/1987 | Dove | 128/69 |

FOREIGN PATENT DOCUMENTS

| | | | |
|---|---|---|---|
| 2649042 | 1/1978 | Fed. Rep. of Germany .... | 128/92 B |
| 654251 | 3/1979 | U.S.S.R. ............... | 128/69 |

OTHER PUBLICATIONS

Harrington: Zimmer Catalog, Warsaw, Ind. 46580, Feb. 1973; pp. D58-65 and 67-71.

Primary Examiner—Clyde I. Coughenour
Attorney, Agent, or Firm—Robert E. Harris

[57] ABSTRACT

A dorsally placed transacrally fixed surgical implant is described for correcting and supporting the spinal column with the implant being particularly useful for aligning and stabilizing the lumbosacral junction. Direct sacral fixation is achieved utilizing a contoured metallic base plate that is firmly fixed to the sacrum by means of a plurality of screws, which screws are angularly disposed with respect to one another to maximize retention of the base plate on the sacrum. A pair of spine engagable rods, contoured to the desired spinal column configuration, have one end inserted into sockets on the base plate with the rods being locked against rotation or other movement relative to the base plate. A total fixation system is provided that has flexibility with respect to rod utilizable components, with the rods having bridges, hooks and/or wires spaced along the rods for engagement with vertebrae of the spinal column to hold the spinal column in the desired position, once achieved, as determined by the contour of the rods.

10 Claims, 5 Drawing Sheets

Fig_11

Fig_10

Fig_12

Fig_13

Fig_14

Fig_15

Fig_16

Fig_17

Fig_18    Fig_19

Fig_20

Fig_21

Fig_22

Fig_23

4,773,402

DORSAL TRANSACRAL SURGICAL IMPLANT

This is a continuation of application Ser. No. 775,650 filed Sept. 13, 1985, now abandoned.

FIELD OF THE INVENTION

This invention relates to a surgical implant and, more particularly, relates to a dorsal transacral surgical implant.

BACKGROUND OF THE INVENTION

Surgical implants are well known, and such implants have been heretofore used as spinal fixation devices in correcting deviations of the spinal column, including scoliosis.

Prior known devices for surgical implants have included the use of a pair of spinal rods for aligning a spinal column (see, for example, U.S. Pat. No. 4,369,769), and have also included rods having hooks or the like thereon engagable with vertebrae of the spinal column to achieve spinal alignment (see, for example, U.S. Pat. Nos. 4,361,141; 4,382,438; 4,404,967; 4,369,770; and 4,085,744). In addition, hook devices with locking means for securing hooking devices to a rod have heretofore been suggested in conjunction with surgical implants (see, for example, U.S. Pat. No. 4,433,676).

Spinal implants have heretofore, however, not been found to be completely satisfactory, at least for some applications, due, for example, to inability of the implant to resist rotation, inability of the implant to sufficiently stabilize the spinal column, and/or inability of the implant to maintain the structural integrity of the implant over a period of time.

It is also been heretofore suggested that screws could be utilized in connection with spinal implants (see, for example, U.S. Pat. No. 4,041,939), and a sacral anchor has been heretofore suggested for a surgical implant for use in correction of scoliosis (see, for example, U.S. Pat. No. 4,047,523).

There still remains, however, a need for an improved surgical implant, including a firmly anchored implant for satisfactory aligning and stabilizing the spinal column, and particularly the lumbosacral junction.

SUMMARY OF THE INVENTION

This invention provides an improved surgical implant for correcting and supporting the spinal column. The implant includes a base plate directly mounted on the sacrum for firmly anchoring a pair of rods extending therefrom, which rods have securing elements thereon engagable with vertebrae of the spinal column to be corrected for causing the spinal column ot assume a contour similar to that of the particular rods utilized. The rods are locked in sockets on the base plate and the securing elements are locked on the rods to assure against independent movement, including rotation, and with the resulting device having sufficient structural integrity to stabilize the spinal column and remain intact over long periods of use.

It is therefore an object of this invention to provide an improved surgical implant.

It is another object of this invention to provide an improved surgical implant for correction and support of a spinal column.

It is another object of this invention to provide an improved surgical implant that is dorsally placed and transacrally fixed.

It is another object of this invention to provide an improved surgical implant that is useful for aligning and stabilizing the spinal column and particularly the lumbosacral junction.

It is another object of this invention to provide an improved surgical implant that includes a base plate fixed to the sacrum and a pair of rods received in sockets on the base plate.

It is another object of this invention to provide an improved surgical implant that includes a pair of spaced rods having securing means engagable with vertebrae of the spinal column to align and stabilize the spinal column. It is another object of this invention to provide an improved method for implanting a spinal correction and supporting device that is to be dorsally placed and transacrally fixed.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figures 1, 2, 3, 4, 5, 6, 7, 8, 9:
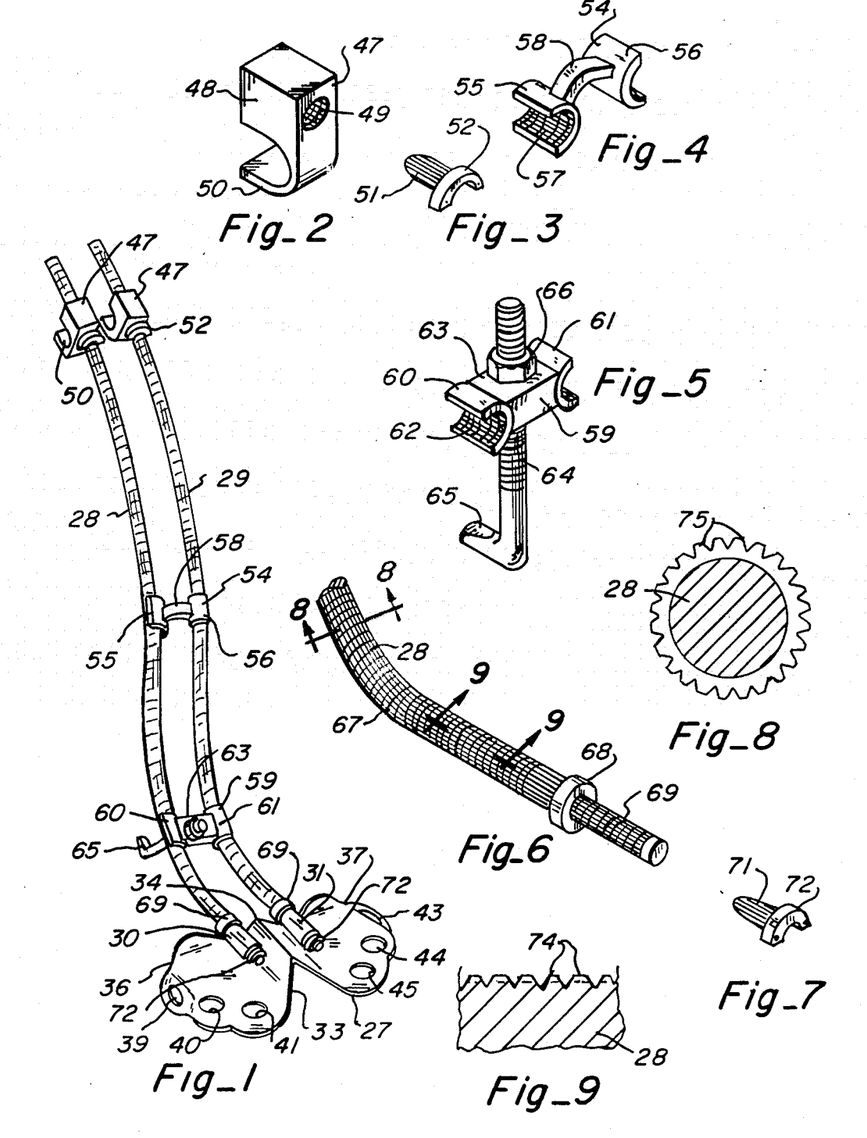
FIG. 1 is a perspective view of the surgical implant of this invention.
FIG. 2 is a perspective view of the hook element shown in FIG. 1.
FIG. 3 is a perspective view of the wedge used to lock the hook element onto a rod as shown in FIG. 1.
FIG. 4 is a perspective view of a bridging element as shown in FIG. 1.
FIG. 5 is a perspective view of a yoke and foot element as shown in FIG. 1.
FIG. 6 is a partial perspective view of the lower portion of one of the rods as shown in FIG. 1.
FIG. 7 is a perspective view of the wedge used for locking the rod in the socket in the base plate as shown in FIG. 1.
FIG. 8 is a cross-sectional view of the rod taken through lines 8—8 of FIG. 6.
FIG. 9 is a partial sectional view of the rod taken through lines 9—9 of FIG. 6.

To achieve a satisfactory implant, this invention utilizes, as shown in FIG. 1, a base plate 27 having a pair of rods 28 and 29 received in sockets 30 and 31, respectively, mounted on the base plate.

Base plate 27 is preferably a contoured, slightly malleable implant made from stainless steel (as are all other components utilized in the implant). The center portion 33 of the base plate has an upwardly extending ridge 34 thereat with sockets 30 and 31 being positioned parallel to and along the opposite sides of the ridge. Sockets 30 and 31 are tubular sections which are fastened to the top side of the base plate in a conventional manner, such as, for example, by welding.

Projections, or wings, 36 and 37 extend outwardly from center portion 33 and each projection has three apertures thereon (designated as apertures 39, 40 and 41 in projection 36 and apertures 43, 44 and 45 in projection 37) formed near the outer edges, which edges are shown curved at the front portion (at apertures 39 and 43). It is to be realized, however, that the curvature of the base plate, depends upon the particular sacrum and-/or particular fixation to be utilized, as brought out more fully hereinafter.

Rods 28 and 29 are also preferably formed of stainless steel, and are contoured as needed for each particular application. The system is a total system, and may utilize one or more types of securing elements for securing vertebrae of the spinal column along the rods.

As shown in FIG. 1, by way of example, each rod 28 and 29 may have a hook element 47 thereon, which hook element, as shown in FIGS. 1 and 2, includes a body portion 48 having a bore 49 therethrough through which the associated rod extends with the bore being slightly larger than the diameter of the rod to enable free axial and rotational movement of the rod in the bore. Hook portion 50 extends below the body portion, and, as shown in FIG. 3, a tapered wedge 51 with head 52 thereon, is utilized to engage the rod extending through the bore to lock the hook element against movement (including precluding rotation and axial movement) independently of the rod. As indicated in FIGS. 2 and 3, bore 49 and wedge 51 are lengthwise serrated, to that upon final placement, sufficient pressure can be applied to cold weld the components in position.

Rods 28 and 29 are maintained in spaced relationship with respect to one another by use of bridging element 54, as shown in FIGS. 1 and 4. As shown, bridging element 54 includes outwardly facing arcuate sections 55 and 56 (the inner surfaces 57 of which are lengthwise serrated) having a V-shaped strut 58 therebetween, with the inner surfaces 57 of arcuate sections 55 and 56 engaging the inner portions of rods 28 and 29 when the bridging element is positioned between the rods, as indicated in FIGS. 1, 10, 20 and 21 of the drawings.

As shown in FIGS. 1 and 5, a yoke and foot element 59 may also be placed between rods 28 and 29. Element 59 includes a pair of outwardly facing arcuate sections 60 and 61 (the inner surfaces 62 of which are lengthwise serrated) at opposite sides of block 63 with the inner surfaces 62 of the arcuate sections 60 and 61 being engagable with the inner portions of rods 28 and 29 when positioned between the rods, as shown in FIGS. 1, 10, 18 and 19 of the drawings. Block 63 has a bore therethrough for receiving a threaded shank 64, which shank has a foot, or hook, 65 at one end. As indicated, foot 65 is tapered toward the front, or freely extending edge, of the foot to facilitate insertion adjacent to a vertebra or the like.

Shank 64 has nut 66 thereon adjacent to block 63 at the side opposite foot 65 so that upon rotation of nut 66, foot 65 can be drawn toward or moved away from block 63 (or, alternately, the bore of block 63 can be threaded so that the foot is drawn toward or moved away from the block by rotation of the shank, and nut 66 can be used to lock the shank in place with respect to the bore).

Figure 12:
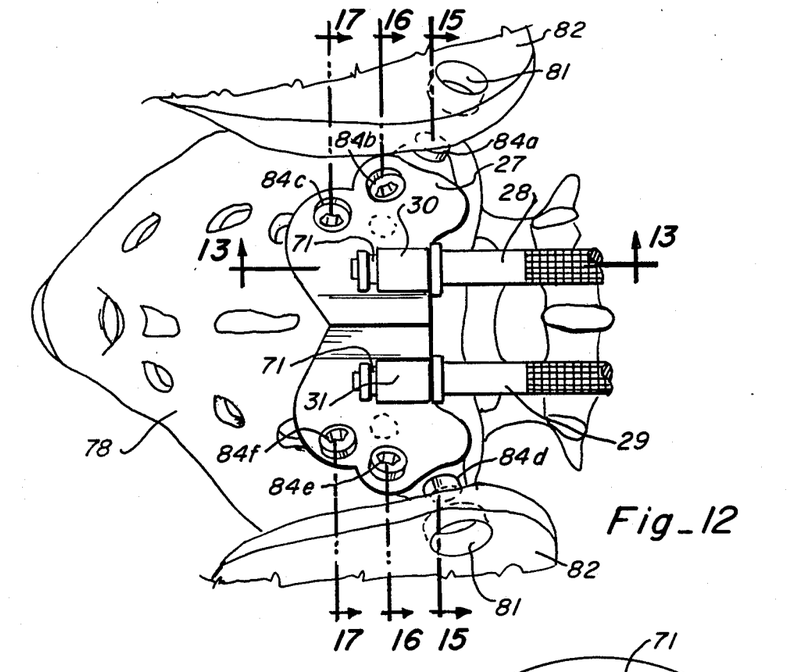
FIG. 12 is a partial lower end view taken through lines 12—12 of FIG. 11 illustrating placement of the base plate on the sacrum.
Figure 13:
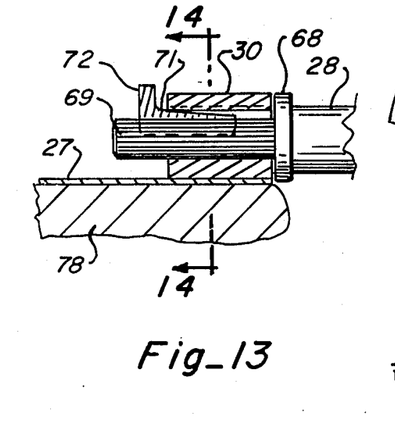
FIG. 13 is a partial sectional view taken through lines 13—13 of FIG. 12 illustrating one of the rods locked in the socket in the base plate.

As shown best in FIG. 6, rod 28 (rod 29 is identical and therefore not separately discussed) has a body portion 67 that terminates at shoulder 68 with a reduced diameter end portion 69 extending therefrom, which end portion is lengthwise serrated and is received in socket 30 (as shown in FIGS. 1, 12 and 13), the inner surface of which is also lengthwise serrated (as is socket 31). A wedge 71 (likewise lenghtwise serrated) having head 72 thereon, as shown in FIGS. 1 and 7, is used to lock the rod in the shaft so that, when so locked, the rod cannot rotate and the rod is therefore constrained to movement with the base plate.

As shown in FIGS. 8 and 9, rod 28 has threads 74 formed thereon, with the threads being flat topped, as indicated in FIG. 9, to lessen the cut into the rod so as to maintain maximum strength, and each thread has lengthwise serrations 75 therein. The threads are 20 per inch which allows small changes in the locking points for the securing elements along the rods (of about 1 mm).

Figure 10:
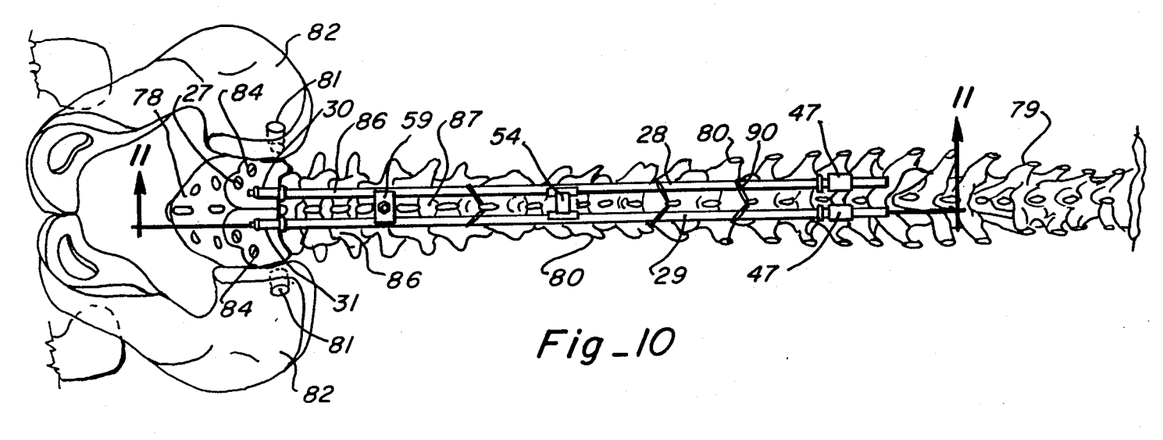
FIG. 10 is a rear view showing the surgical implant of this invention in place to support and correct a typical spinal column.
Figure 11:
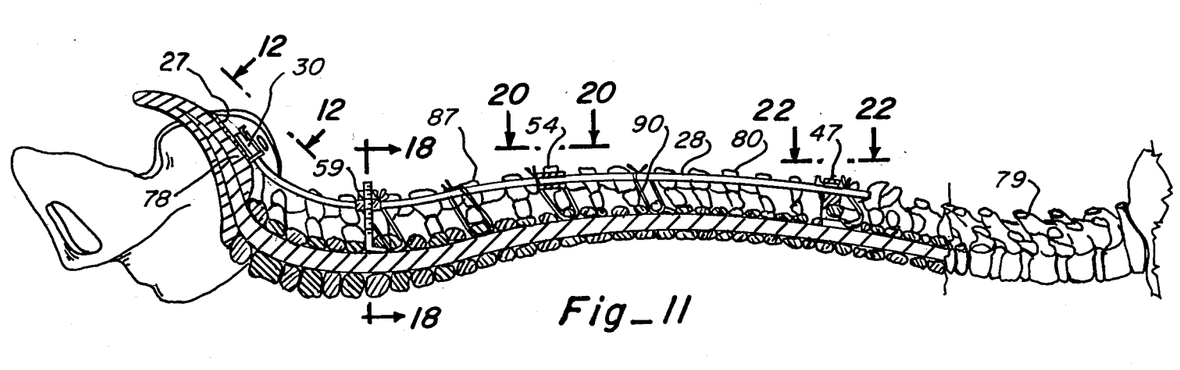
FIG. 11 is a side view taken through lines 11—11 of FIG. 10 illustrating the alignment and support provided by the implant.

Typical use of the implant of this invention is shown in FIGS. 10 and 11. It is meant to be emphasized that while only one bridging element, yoke and foot element, and hook element has been shown in FIGS. 10 and 11, any number of each could be utilized as might be needed for a particular application. In addition, the use of wire could be expanded, and pedicle screws (not shown) could also be utilized.

Figure 14:
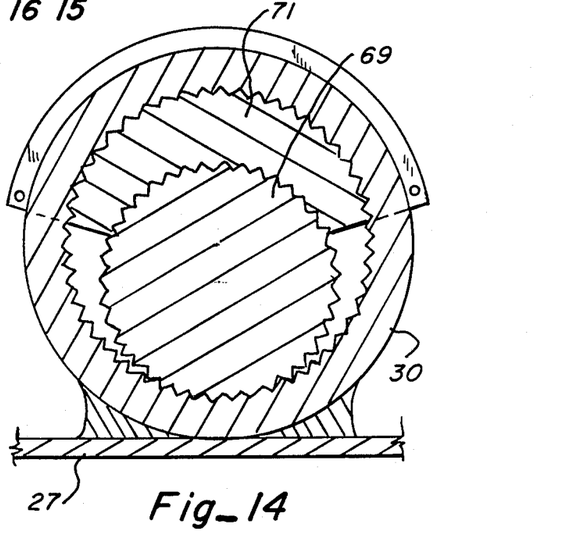
FIG. 14 is a cross-sectional view taken through lines 14—14 of FIG. 13 illustrating locking of the rod in the socket by the wedge.

As shown in FIGS. 10 and 11, base plate 27 is mounted on sacrum 78 of the spinal column 79 of the body and contoured rods 28 and 29, when positioned in sockets 30 and 31 (as shown in FIGS. 12 through 14), extends along the vertebrae 80 of spinal column 79 so that such vertebrae can be secured to rods 28 and 29 to cause alignment of the spinal column and thereafter support the aligned spinal column in the manner generally dictated by the contour of the rods.

The sacrum offers several possibilities for fixation, which, when combined, appear to provide a secure foundation for a dorsally placed transacrally fixed implant. The dorsal sacral landmarks, and particularly the first and second dorsal foramina, are readily identifiable and relate in a consistent manner both qualitatively and quantitatively to the major mass of the sacral bone, which is located ventrally to the vital structures of the sacrum.

Ideal lumbosacral fixation should secure directly to the sacrum rather than indirectly by way of the iliae, and be modular for ease of insertion, versatile to allow use in a wide variety of diseases and deformities, and integratable with existing and evolving cephalad spine implants. The sacral foundation of this invention provides a dorsal sacral implant that is secured ventrally by multiple transacral anchors.

To determine the best configuration for such a sacral implant, implant configuration and transacral fixation site possibilities were first studied on a variety of anatomical models and four embalmed cadaver specimens. To study contour, plaster of Paris negative and laminated paper positive molds were prepared and from these 0.5 mm (0.02 inch) thick stainless steel prototypes were prepared.

To study transacral anchor possibilities, drill holes were placed in six different sites. The placements were selected to safeguard neurovascular structures, avoid sacroiliac articulations, and provide maximum bone fixation. The three dimensional placement of the drill sites was confirmed by Faxitron radiography. The relative strength of fixation site combinations was also estimated in the embalmed human sacrae and in fresh calf sacrae using hand held spring scales.

To study the dimensions of the dorsum of the first two sacral vertebral segments, and the depth of the transacral fixation sites, 18 cadaver sacrae of known sex (9 males and 9 females) and 31 sacrae of unknown sex were measured with calipers. In addition, anthropometric sacral dimensional measurements were determined in the 18 sacrae of known sex. Student t-test and linear correlation coefficient analyses, where appropriate, were also performed.

To study the effect of transitional vertebrae on sacral configuration, 8 sacrae so involved were studied.

The transacral fixation depths and dorsal sacral measurements of the 18 sacrae of known sex are tabulated in Tables 1 and 2 as follows:

TABLE 1

| TRANSACRAL FIXATION (TSF) DEPTH | | | |
|---|---|---|---|
| | Distance (mm) | | |
| | Males (9) | Females (9) | P |
| TSF 1 | 49.7 (±3.7) | 46.9 (±3.3) | NS |
| TSF 2 | 38.8 (±2.7) | 37.2 (±2.5) | NS |
| TSF 3 | 30.7 (±3.1) | 28.8 (±2.3) | NS |

TABLE 2

| HUMAN SACRUM: DORSAL MEASUREMENTS | | | |
|---|---|---|---|
| | Distance (mm) | | |
| | Males (9) | Females (9) | P |
| S1DF to S1DF | 48.8 (±5.0) | 47.4 (±3.8) | NS |

TABLE 2-continued

| HUMAN SACRUM: DORSAL MEASUREMENTS | | | |
|---|---|---|---|
| | Distance (mm) | | |
| | Males (9) | Females (9) | P |
| S2DF to S2DF | 43.1 (±4.2) | 44.0 (±3.0) | NS |
| S1DF to S2DF | 26.2 (±2.4) | 21.4 (±2.5) | <.001 |
| SN to S1DF | 21.7 (±2.3) | 22.3 (±1.6) | NS |

LEGEND:
S1DF = First Sacral Dorsal Foramen
S2DF = Second Sacral Dorsal Foramen
SN = Superior Sacral Notch of the Sacral ALA The longest, and apparently most secure, transacral fixation site was previously described by Harrington and Dixon (Harrington, P. R. and Dixon, J. H. "Spinal instrumentation in the treatment of severe progressive spondyloisthesis", Clin. Orthop. 117:157–163, 1976) and passes through the first sacral pedicle to the sacral prominatory (TSF 1).

The dorsal entry point is caudad and lateral to the superior facet, 10 mm lateral and five mm cephalad from the first sacral dorsal foramen. The direction with reference to a staring line perpendicular to the flat dorsal surface of the first and second sacral laminae was 15 degrees cephalad in the frontal plane, 20 degrees cephalad in the sagittal plane, and 35 degrees medially in the horizontal plane.

Access to the entry site necessitated a dowel cut window 81 in the iliac crest 82 (as indicated in FIG. 10). The TSF 1 depth was 49.7 mm (±3.7) in the nine males and 46.9 mm (±3.3) in the nine females. It was not significantly different than the distance between the outer edges of the first sacral dorsal foraminae (S1—S1) which was 48.8 mm (±5.0) in males and 47.4 mm (±3.8) in females.

The distance from the superior sacral notch of the sacral ala to the cephalad edge of the first dorsal sacral foramen was similar for males, 21.7 mm (±2.3) and females, 22.3 mm (±1.6). The distance between the cephalad edges of the first and second dorsal sacral foramina was significantly shorter in females, 21.4 mm (±2.5), than in males, 26.2 mm (±2.4), (p <.001).

A common measurement used to separate male and female sacrae, a ratio of the transverse diameter of the first sacral body to the breadth of the sacrum, was not significantly different, males 41.9 (±3.2), and females 39.8 (±3.3), as shown in Table 3 as follows:

TABLE 3

| HUMAN SACRUM: CEPHALAD EDGE MEASUREMENTS | | | |
|---|---|---|---|
| | DISTANCE | | |
| | MALES (9) | FEMALES (9) | |
| TRANSVERSE DIAMETER S1 BODY (TB) | 43.7 mm (±3.9) | 42.4 mm (±4.4) | NS |
| ANTERIOR BREADTH AT S1 (BRD) | 104.0 mm (±6.9) | 106.4 mm (±4.7) | NS |
| TB/BRD × 100 | 41.9 (±3.2) | 39.8 (±3.3) | NS |

The distance between the outer edges of the second dorsal sacral foramina was similar, males 43.1 mm (±4.2) and females 44.0 mm (±3.0).

Of the five additional transacral fixation sites studies, two appear superior. One (TSF 2) transversed from the first sacral transverse tubercle to the lateral mass of the sacrum. The direction with reference to a staring line perpendicular to the flat dorsal surface of the first and second sacral laminae was 25 degrees cephalad in the frontal plane, 25 degrees cephalad in the sagittal plane, and 25 degrees lateral in the horizontal plane. This distance was similar for males, 38.8 mm ($\pm 2.7$), and females, 37.2 mm ($\pm 2.5$).

The other site (TSF 3) passed from a point midway between the intermediate and lateral sacral crest and midway between the first and second dorsal foramina to the lateral mass. The TSF 3 direction with reference to a starting line perpendicular to the flat dorsal surface of the first and second sacral laminae was 20 degrees caudad in the frontal plane, five degrees caudad in the sagittal plane, and 50 degrees lateral in the horizontal plane. This distance was similar for males, 30.7 mm ($\pm 3.1$) and females, 28.2 mm ($\pm 2.3$).

For the 49 normal sacrae studied, without regard to sex, there was a positive correlation between the first sacral dorsal interforaminal distance and TSF 1 depth ($p < 0.001$), between TSF 1 depth and TSF 2 depth ($p < 0.005$), and between TSF 1 depth and TSF 3 depth ($p < 0.001$), as shown in Table 4 as follows:

TABLE 4

| DORSAL AND TRANSACRAL FIXATION SITE MEASUREMENT CORRELATIONS: WITHOUT REGARD TO SEX (N = 49) | | |
|---|---|---|
| | | P |
| S1DF—S1DF vs. TSF 1 | .5297 | <.001 |
| TSF 1 vs. TSF 2 | .4137 | <.005 |
| TSF 1 vs. TSF 3 | .5294 | <.001 |

LEGEND:
S1DF = FIRST SACRAL FORAMEN
TSF = TRANSACRAL FIXATION

There were eight sacrae with transitional vertebrae, five had complete sacralization of L5 with the lateral mass appearing to coincide with the "new" S1 vertebrae, and three had imcomplete sacralization of L5 and the lateral mass coincided with the true S1 vertebrae. In these, as well as in the one sacrum with complete lumbarization of S1, the TSF 1 distance was relatively short.

Although there are significant sex and race related differences in the anthropometry of the human sacrum, these differences are small, approximately 5 to 6 mm. In the study, for the implant of this invention, the major sex difference was not in the S1 body/sacral breadth ratio, but in the spacial relations of the first and second dorsal sacral foramina, the distance being shorter in females. However, the relatively large S1 pedicle approach to the prminatory appears to offer adequate compensation for this difference in an implant with fixed distance fixation entry sites. While interracial differences were not considered, they appear to be less significant than the intersex differences. Thus, design of sacral implants based on sex and race differences does not appear to be necessary.

As a result of these studies, the dorsal sacral implant of this invention has been designed to meet the implant needs and requirements for sacral fixation.

Figure 15:
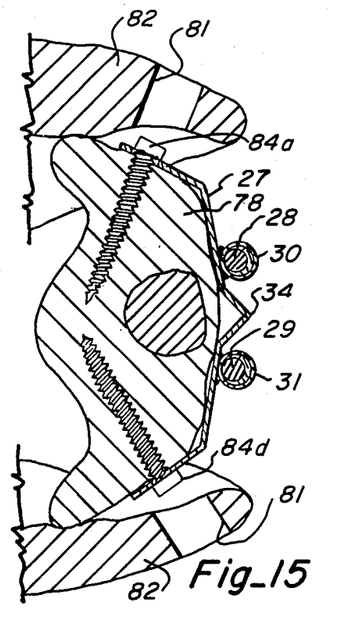
FIG. 15 is a partial sectional view taken through lines 15—15 of FIG. 12 illustrating TSF 1 screw placement in the sacrum.
Figure 16:
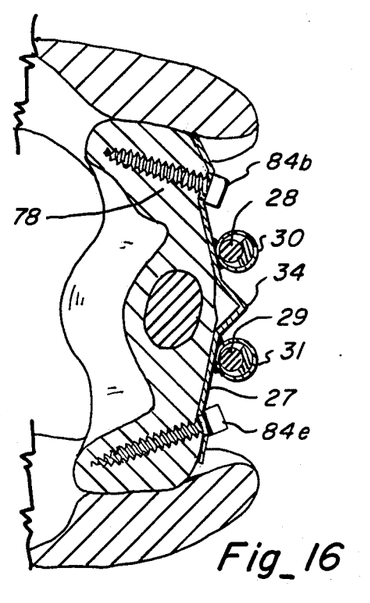
FIG. 16 is a partial sectional view taken through lines 16—16 of FIG. 12 illustrating TSF 2 screw placement in the sacrum.
Figure 17:
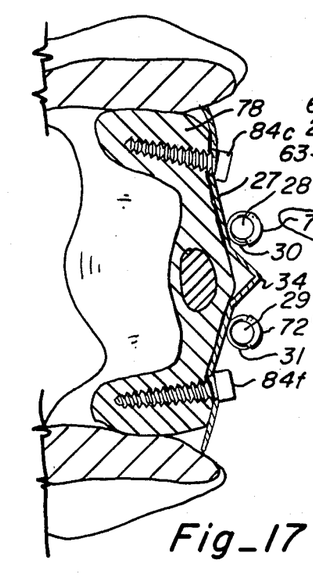
FIG. 17 is a partial sectional view taken through lines 17—17 of FIG. 12 illustrating TSF 3 screw placement in the sacrum.
Figure 18:
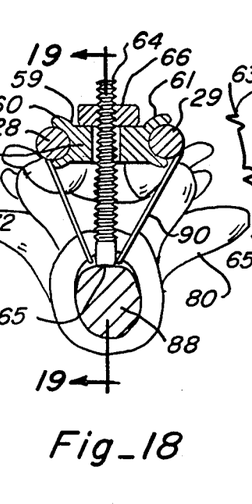
FIG. 18 is a sectional view taken through lines 18—18 of FIG. 11 illustrating the yoke and foot element with the foot portion engaging vertebrae to facilitate alignment of a spinal column.
Figure 19:
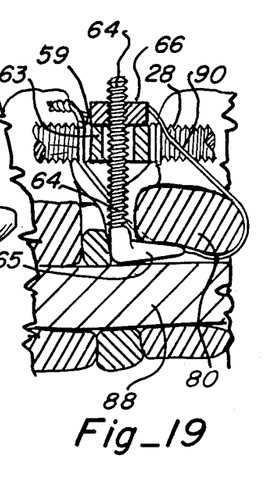
FIG. 19 is a partial sectional view taken through lines 19—19 of FIG. 18.
Figure 20:
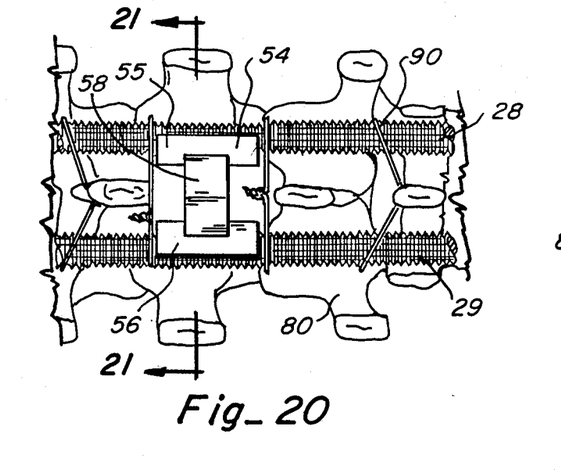
FIG. 20 is a partial sectional view taken through lines 20—20 of FIG. 11 illustrating use of a bridging element and associated wiring utilizable in aligning a spinal column.
Figure 21:
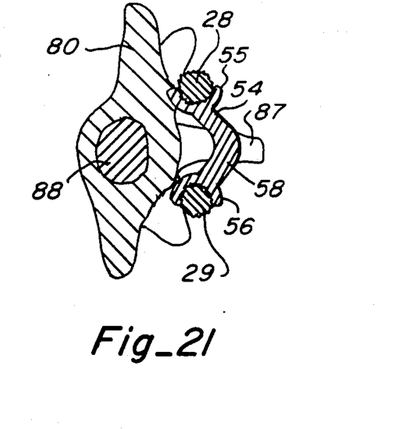
FIG. 21 is a partial sectional view taken through lines 21—21 of FIG. 20.
Figure 22:
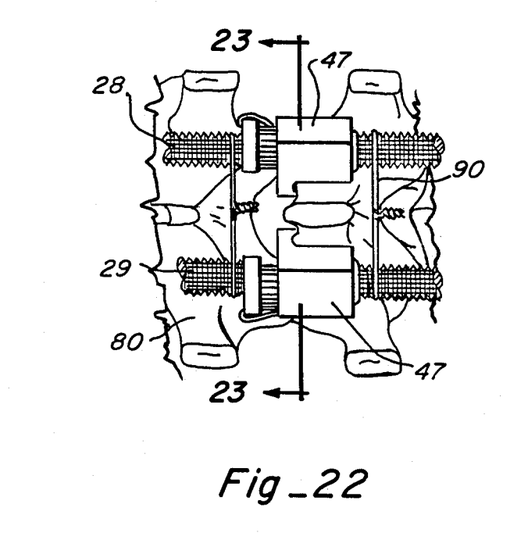
FIG. 22 is partial sectional view taken through lines 22—22 of FIG. 11 illustrating use of a hook element to engage vertebrae.
Figure 23:
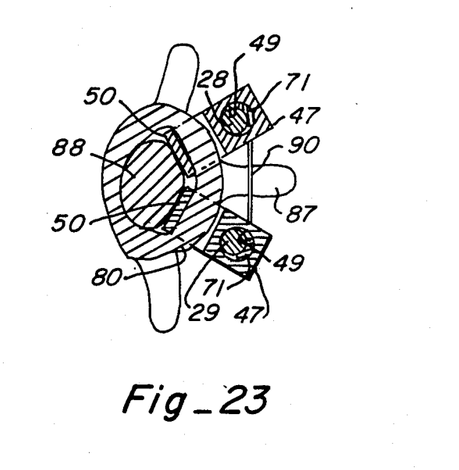
FIG. 23 is a partial sectional view taken through lines 23—23 of FIG. 22.

To achieve sacral fixation, base plate 27 is secured on sacrum 78 by means of screws 84 (are more specifically designated as screws 84a-84f as shown best in FIGS. 12, 15, 16 and 17). The positioning of screws 84a and 84d are best shown in FIGS. 12 and 15, while the positioning of screws 84b and 84c are best shown in FIGS. 12 and 16, and the positioning of screws 84c and 84f are best shown in FIGS. 12 and 17. As can be appreciated from FIGS. 12 and 15 through 17, the screws are placed in a three-dimensional configuration in the sacrum with the location and angles being predetermined, as brought out hereinabove, to provide maximum retention of the base plate on the sacrum even though severe forces might be later applied thereto.

After the base plate is fixed to the sacrum, and after the rods are contoured to the desired contour needed for the particular subject, the rods are placed in sockets 30 and 31 and when so placed, wedges 71 are driven into the space between the rods and sockets as shown in FIGS. 13 and 14, with the serrated surfaces maintaining the wedges in place (preferably the wedges are wired in place to give even more protection against dislodging by later patient movements).

The body, or main, portions of rods 28 and 29 are utilized to secure spinal column 79 in the desired position and alignment dependent upon the curvature of the rods, with the vertebrae of the spinal column being secured to the rods as generally shown in FIGS. 10 and 11, and as more specifically shown in FIGS. 18 to 23. As shown, rods 28 and 29, when finally positioned, are adjacent to the lamina 86 of vertebrae 80 of spinal column 79 with the rods having the spinous process 87 of the vertebrae between the rods.

As shown, hook elements 47 on rods 28 and 29 are utilized to engage vertebrae 80 of spinal column 79 with hooks 50 engaging the underside of a vertebra (above spinal cord 88) to maintain the vertebrae adjacent to the rods. Bridging elements 54 maintain rods 28 and 29 spaced, and vertebrae can be held in place adjacent to the spacing elements by wire 90, as needed. As shown, wire 90 may also be wrapped around rods 28 and 29 and bridging elements 54 as needed for maintaining the positioning of the bridging elements. Yoke and foot elements 592 are utilized with foot 65 hooked under a vertebra 80 so that the vertebrae can be lifted or otherwise moved toward the rods by lengthening or shortening the shank relative to the spacer block. All removable elements (including wedges) are preferably wired in place upon final implant to assure against loosening and/or loss of any such element or component from its intended position.

In performing the surgical implant, the sacral anatomy is preferably first defined, after which staged surgery (anterior disectomy and fusion if necessary to restore alignment and/or provide stabilization) may be carried out prior to sacral fixation.

To prepare the sacral fixation, the sacrum is first exposed, measurements are then taken for determining the best positioning of the base plate on the sacrum, the site is thereafter prepared and sculptured, and the TSF 3 holes in each side of the base plate are located and drilled (25 mm ). The iliac crest entry portals are next located and drilled as necessary to provide the portals, and the TSF 1 holes are then located and drilled (45 mm ). The base plate is next placed into position on the sacrum, the TSF 2 holes are confirmed over the S1 transverse tubercle, the TSF 1 are then drilled, and screws are securely screwed into all of the drilled holes.

After fixation of the base plate, lumbar and thoraco-lumbar fixation is carried out by selecting the correction mode to be utilized (distraction, compression, extension, flexion, rotation, or combination), preparing the proximal fixation sites, contouring the rods and placing the rods in the sockets of the base plate, wedging the rods in the desired position, and then placing the necessary securing elements on the rods to enable the spinal column to be secured in the desired shape by means of the hooks and/or wire utilized (with various instruments being utilized, as necessary, to facilitate the fixation). As an operation proceeds, the various securing elements used as hooks can be adjusted by removing the tapered wedges, where necessary, by utilizing the heads on the wedges to easily withdraw the wedges, and then moving the elements, after which the elements are again screwed in place. The hooks can, of course, be placed for compression or distraction.

It is meant to be realized, that various elements and/or method steps as described herein, could be modified as would be obvious to one skilled in the art without departing from the intended scope of this invention.

As can be appreciated from the foregoing, this invention provides an improved surgical implant and method that utilizes direct sacral fixation.

What is claimed is:

1. An implantable support and correction device for a spinal column, said device comprising:
   base means having a central portion and first and second mounting portions with said first and second mounting portions having first fastening means for enabling fastening of said base means directly to the sacrum of the spinal column of a body, and said first and second mounting portions each including second fastening means at said central portion and adjacent to said first fastening means and locking means at said second fastening means;
   a pair of elongated rods each of which has a main portion shaped in the configuration desired for correction of said spinal column, and each of which rods has an end portion configured to be mounted in and secured to said second fastening means of said base means so that, when said base means is fastened to said sacrum and said rods are mounted and secured to said second fastening means, said end portion of each of said rods is effectively fastened to said sacrum at positions adjacent to said first and second mounting portions of said base means with each of said rods being locked into position by said locking means so that each of said rods is thereafter maintained in fixed position relative to one another and to said base means to thereby provide a firm foundation for aligning and stabilizing the lumbosacral junction with that said main portion of each of said rods being maintained adjacent to that part of the spinal column to be corrected and with each of said rod means being at the opposite sides of vertebrae of said spinal column; and
   a plurality of securing means positioned along said main portion of said rods and adapted to engage said spinal column so that said spinal column is caused to substantially assume the shape of the main portion of said rods.

2. The device of claim 1 wherein said securing means includes at least one of hook means having one part engageable with vertebrae of said spinal column and bridging means connected between said rods.

3. The device of claim 2 wherein said securing means includes at least yoke and foot means having a threaded shaft with a foot extending therefrom to provide said hook means, with said yoke and foot means also including bridging means having threaded means for receiving said threaded shaft whereby rotation of said shaft in one predetermined direction relation to said bridging means causes said hook means to be moved toward said rods.

4. An implantable support and correction device for a spinal column, said device comprising:
   base means having a central portion with first and second sockets formed thereon, and first and second mounting portions extending outwardly in different directions from said central portion with said first and second mounting portions each having a plurality of spaced apertures therein for enabling said base means to be securely and directly fastened by means of screws extending through said apretures into the sacrum of the spinal column of a body;
   a pair of elongated rods each of which has a main portion shaped in the configuration desired for correction of said spinal column, and an end portion configured to be fastened in said sockets with each end portion being received in different ones of said sockets so that, when said base means is fastened to said sacrum and said rods are fastened in said sockets, said end portion of each of said rods is effectively fastened to said sacrum at positions adjacent to said apertures in said base means and the main portion of each of said rods is adjacent to at least that part of said spinal column that is to be corrected by said rods;
   locking means engagable with said base means and said end portions of said rods for constraining said rods to common movement in conjunction with one another and with said base means to thereby provide a firm foundation for aligning and stabilizing the lumbosacral junction; and
   a plurality of securing means connected with said main portion of each of said rods and adapted to engage vertebrae of said spinal column to cause said spinal column to assume the shape of the main portion of said rods to thereby correct and support said spinal column.

5. The device of claim 4 wherein said base means is formed from a thin metallic sheet having a raised center portion with said sockets mounted at opposite sides of said raised portion.

6. The device of claim 4 wherein said screws extending through said apertures into said sacrum are angled with respect to one another when inserted into said sacrum to achieve maximum strength of retention of said base means on said sacrum.

7. The device of claim 6 wherein said first and second mounting portions each have three apertures therein for mounting of said base means on said sacrum by means of six screws.

8. The device of claim 4 wherein said main portions of each of said rods is threaded and said end portion of each of said rods is serrated, and wherein the inner surfaces of said sockets and surfaces of said securing means engaging said main portion of said rods are serrated to facilitate maintaining the desired orientation of said rods and said sacrum means with respect to said base means and said spinal column.

9. The device of claim 8 wherein said locking means includes a wedge having a serrated tapering portion received into each said socket between the walls of said socket and said end portion of said rod within said socket.

10. The device of claim 8 wherein said securing means includes hook means having one part engagable with a vertebra of said spinal column and another portion having a bore therein for receipt of an associated one of said rods therethrough with said bore having a diameter slightly larger than the diameter of said rod received therein, and wherein said securing means includes a wedge having a tapered serrated portion inserted between the wall of said bore and said rod received therein to fix the positioning of said securing means relative to said rod.

* * * * *